United States Patent [19]

Greiner

[11] Patent Number: 5,183,663

[45] Date of Patent: Feb. 2, 1993

[54] TREATING SKIN LESIONS

[75] Inventor: Richard W. Greiner, Kennett Square, Pa.

[73] Assignee: Hercules Incorporated, Wilmington, Del.

[21] Appl. No.: 362,800

[22] Filed: Jun. 7, 1989

[51] Int. Cl.$^5$ ............................................. A61F 13/00
[52] U.S. Cl. .................................... 424/443; 424/444; 424/448; 424/449
[58] Field of Search ............... 424/443, 448, 449, 478, 424/78

[56] References Cited

U.S. PATENT DOCUMENTS

| | | | |
|---|---|---|---|
| 2,272,397 | 2/1942 | Becher et al. | 514/311 |
| 2,272,399 | 2/1942 | Becher et al. | 514/259 |
| 3,439,676 | 4/1969 | Burda | 604/290 |
| 3,698,392 | 10/1972 | Vogt et al. | 424/446 |
| 3,755,218 | 8/1973 | Yen et al. | 523/112 |
| 4,046,725 | 9/1977 | Pusineri | 523/112 |
| 4,116,898 | 9/1978 | Dudley et al. | 523/112 |
| 4,377,010 | 3/1983 | Fydelor et al. | 623/1 |
| 4,433,072 | 2/1984 | Pusineri et al. | 523/105 |
| 4,452,776 | 6/1984 | Refojo | 424/81 |
| 4,460,369 | 7/1984 | Seymour | 424/448 |
| 4,496,535 | 1/1985 | Gould et al. | 424/402 |
| 4,542,169 | 9/1985 | Costerton | 523/121 |
| 4,563,184 | 1/1986 | Korol | 604/368 |
| 4,598,006 | 7/1986 | Sand | 424/81 |
| 4,678,684 | 7/1987 | Sand | 424/213.36 |
| 4,720,512 | 1/1988 | Hu et al. | 513/112 |
| 4,725,279 | 2/1988 | Woodruff | 424/448 |
| 4,788,061 | 11/1988 | Shore | 424/448 |

OTHER PUBLICATIONS

"Polymeric Delivery Systems for Controlled Drug Release", Langer, *Chem. Eng. Commun.*, vol. 6, pp. 1–48, 1980.

"Present and Future Applications of Biomaterials in Controlled Drug Delivery Systems", *Biomaterials* vol. 2 (1981), pp. 201–214.

Primary Examiner—Thurman K. Page
Assistant Examiner—Leon R. Horne
Attorney, Agent, or Firm—Wegner, Cantor, Mueller & Player

[57] ABSTRACT

Disclosed is a method of treating a skin lesion comprising applying to the lesion a dry bandage comprising a gas- and moisture-permeable, flexible, thermoplastic film impregnated with a pharmaceutical.

1 Claim, 2 Drawing Sheets

TREATING SKIN LESIONS

The present invention relates to a method of treating skin lesions using pharmaceutical delivery systems. In particular, it relates to the treatment of decubitus ulcers.

Skin lesions present two concurrent challenges—promoting healing and preventing infection. Healing is a complex process involving three general phases: inflammation, granulation tissue formation, and matrix formation and remodeling. If the lesion becomes infected, inflammation will persist and interfere with the next phase of healing, i.e., granulation tissue formation. Accordingly, both increasing the speed of healing to avoid infection, and preventing infection to avoid interference with healing, are advantageous goals in the treatment and prevention of skin lesions.

In particular, decubitus ulcers, also known as trophic ulcers, pressure sores, and bed sores, are recurrent problems, which arise when pressure is applied to localized skin areas over an extended time. Resulting shear and compression forces effect stopping of blood flow to the localized area, starving the tissue of needed oxygen and nutrients, eventually causing tissue necroses.

Known methods of treating decubitus ulcers include applying therapeutic agents, such as cleansers, ointments, creams, antiseptics, and enzymes, covering the ulcer with known dressings, such as gauze and occlusive films, and incorporating antibiotics in pressure-sensitive adhesives coating solid thermoplastic bandages. Growth factors derived from blood platelets are known to have been topically applied to decubitus ulcers, effecting increased healing rates.

Accordingly, the present invention is a method of treating a skin lesion comprising applying to the lesion a dry bandage comprising a gas- and moisture-permeable, flexible, thermoplastic film impregnated with a pharmaceutical. (For the purposes of this invention, the term "dry" refers to the absence of superficially detectable liquid within the bandage.) Release from the film of impregnated pharmaceuticals, such as antibiotics, to the lesion and surrounding tissues aids in healing the lesion and in inhibiting further tissue damage. The present invention is also a method of treating a skin lesion comprising applying a vasodilator to the lesion.

Figure 1:
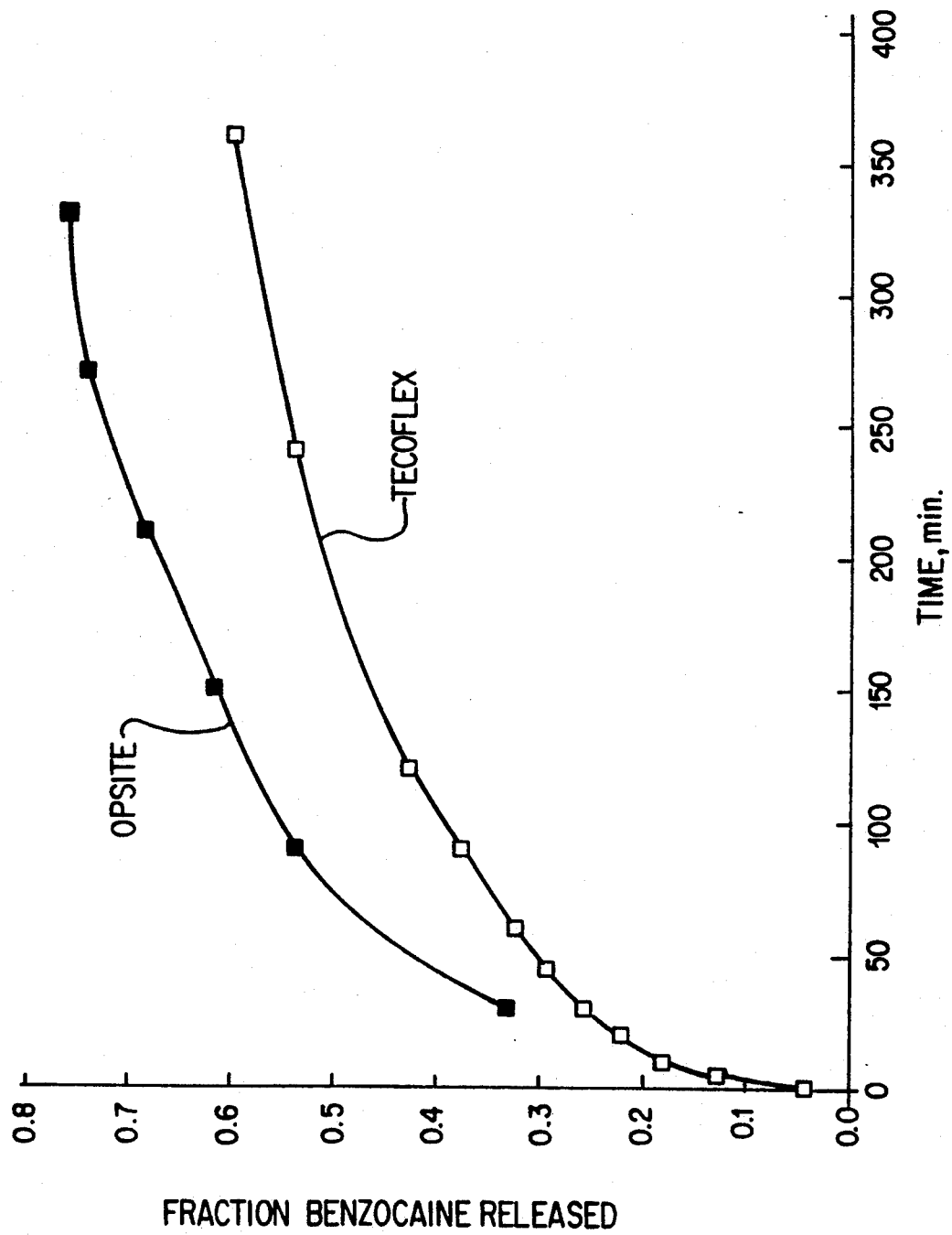
FIGS. 1 and 2 are graphs recording the results of the rate of release of benzocaine from various thermoplastic films.

Thermoplastic films useful in accordance with the present invention are permeable to both gas and moisture to facilitate lesion healing. Solid thermoplastic polymers that are inherently gas- and moisture-permeable are useful to make the film, but ordinarily impermeable, solid, thermoplastic polymers are also useful if cast into microporous films. Inherently permeable, solid, thermoplastic polymers can also be cast as a microporous film in accordance with the present invention, which is particularly useful when pharmaceuticals of relatively large molecular weight and size, such as growth factors, are used. Non-limiting examples of gas- and moisture-permeable, solid thermoplastic polymers are commercially available and include polyurethanes such as disclosed in British Pat. No. 1,280,631, incorporated herein by reference. Polymer materials which are suitable for use in the present invention contain hydrophilic chemical groups and include silicone polymers, polyurethanes, cellulose derivatives, polyether-polyamides, polyamides, and crosslinked polyvinyl alcohols. Materials preferable for use in this application include aromatic polyetherurethanes, polyester elastomers, aliphatic polyetherurethanes (such as Tecoflex TM EG-93A made by Thermedics, Inc.) and polyurethanes (such as polyurethane MP1182 TM (made by J. P. Stephens, Inc.). The use of various copolymers can also be incorporated and include copolymers based on vinyl acetate, vinyl chloride or methyl methacrylate. Non-limiting examples of microporous polymers are commercially available and include polyolefins and polyurethanes.

The thickness of the thermoplastic film varies depending on its intended use and the thermoplastic material and pharmaceutical involved, and is readily determinable by the skilled artisan. The film has a thickness between about 25–500 microns, with a thickness of about 30–100 microns being desirable. Preferably, the film has a thickness between about 40–80 microns. Length and width of the film depend on intended use. Generally, the film has sufficient size to cover the entire skin lesion. Preferable sizes, again depending on use, will be readily apparent to the skilled artisan.

The useful thermoplastic films are preferably impregnated with the pharmaceutical by immersing the film in a saturated solution containing the pharmaceutical dissolved in a pharmaceutically acceptable solvent or more preferably by using a supercritical, pharmaceutically acceptable, swelling agent as a deposition medium as taught in U.S. Pat. No. 4,598,006, the disclosure of which is incorporated herein by reference. Solvents such as water, isopropanol, low molecular weight alcohols (such as methanol, propanol, ethylene glycol and glycerol) and dipolar, aprotic solvents (such as DMSO, DMF, 2,3-butylene carbonate and dimethyltetramethyl sulfone) are contemplated in carrying out this invention. In addition, more viscous solvents or gels are in the contemplated present invention. Viscous solvents include polyethylene glycols with molecular weights between 1,000 and 17,500. Gels such as cross-linked solutions of polyacrylamide, polyvinyl alcohol, hydroxyethyl cellulose, poly(hydroxyethylmethacrylate) or gelatin can be used. Any pharmaceutical that is dissolvable in a pharmaceutically acceptable solvent or highly volatile, pharmaceutically acceptable swelling agent is useful in accordance with the present invention. Useful pharmaceuticals depend on the desired treatment. Non-limiting examples include antibiotics, anti-inflammatory agents, analgesics, anti-fungal agents, topical anesthetics, antiseptics, vasodilators, anti-spasmodic agents, and growth factors, such as methenamine, nalidixic acid, cinoxacin, norfloxacin, pifloxacin, gentamicin sulfate, clindamycin phosphate, benzocaine, triethanolamine salicylate, hydrocortisone, trolamine salicylate, theophylline, dipyridamole, minoxidil, nylidrin hydrochloride, nifedipine, erythrityl nitrate, nitroglycerine, cinepazide, isoxsuprine, trolnitrate phosphate, isosorbide dinitrate, betahistine, pentaerythritol tetranitrate, epidermal growth factor (EGF), transforming growth factors alpha and beta (TGF-alpha and -beta), fibroblast growth factors alpha and beta (FGF-alpha and -beta), cartilage inducing growth factors A and B (CIF-A and -B), tumor angiogenesis factor (TAF), and platelet derived wound healing factors (PDWHF).

The amount of pharmaceutical impregnated into the film depends upon various factors such as length of time desired for administration, the size of the film, film thickness, area of film in contact with the body, solubility of pharmaceutical agent in the film, diffusion rate of the pharmaceutical agent in the film, therapeutic index of the pharmaceutical agent and patient weight and age. The amount of pharmaceutical varies between about 1 and 50% by weight of the film, but generally will be about 5 to 15% by weight. Based upon a standard size patch of film (50 sq. cm., 0.050 mm thick), the amount of pharmaceutical impregnated into the thermoplastic film varies between about 7.5 mg to 4 g.

The impregnated, thermoplastic film is a dry bandage that contacts and covers the skin lesion. The bandage can have various forms and structures, which will be apparent to the skilled artisan. In its simplest form, the bandage is a strip of impregnated thermoplastic film that can be applied to the lesion.

A means for maintaining the bandage in contact with the skin is optionally provided either separate from or as an integral part of the bandage. For example, a layer of adhesive material can be applied to the side of the bandage that opposes the side that will contact the lesion, and the bandage designed of sufficient length to allow it to be wrapped around the affected part of the body and onto itself. Alternatively, an adhesive can be applied to the same side of the bandage that is to contact the lesion, so as to make the bandage adhere to the area of the skin surrounding the lesion.

Suitable adhesives include well known pressure sensitive adhesives that contain a blend of low viscosity polyvinyl ethyl ethers, such as disclosed in British Pat. No. 1,280,631 and copolymers of acrylate ester with acrylic acid, such as disclosed in European Pat. No. 35399. Preferably, any adhesive layer present on the bandage is protected with a removable cover sheet, which can have an adhesive coating to facilitate removal. Still yet, the bandage can merely be a strip of the impregnated film that is long enough to wrap around the affected body part with its ends tied in a knot. Optionally, a backing layer that is impermeable to the pharmaceutical is provided on the side of the bandage apposing the side designed to contact the lesion. Useful backing layers are gas- and moisture-permeable and include materials described in British Pat. No. 1,280,631 and polyurethanes disclosed in European Pat. No. 51935, the disclosures of which are incorporated herein by reference.

Preferably, the bandage is pre-formed into the desired end product before impregnation with the pharmaceutical. This avoids any loss of pharmaceutical that would have occurred during manufacture of the desired article. Commercially available, preformed thermoplastic bandages that can be impregnated with a pharmaceutical in accordance with the present invention include adhesive-backed polyurethane dressings; nylon mesh reinforced, adhesive backed, transparent, aliphatic polyurethane dressings; microporous, linear, low density polyethylene dressings; reinforced, silicone elastomer dressings; and microporous, polyurethane dressings.

The bandage of the present invention can be conveniently contained in a sterilized kit for dispensing. Preferably, the kit is a sterilized wrapper that is impermeable to air, moisture and bacteria. Examples of useful wrappers are metallized pouches or polyolefin bags which can be sterilized by heat treatment or with ethylene oxide. Packaging details are well known to those having ordinary skill in the art.

The following non-limiting examples are provided to more clearly describe the present invention. In the examples all parts and percentages are by weight unless otherwise indicated.

EXAMPLE 1

A commercially available aromatic polyether urethane dressing weighing 0.73 g; having a thickness of 0.05 mm; impermeable to bacteria; 90–99% oxygen permeable at an oxygen partial pressure=38–700 mm Hg; moisture vapor permeable up to 120 $g/m^2/hr$ at high relative humidity (RH) and room temperature (RT); and having an adhesive-backing containing a modified vinylmethylether/maleic anhydride copolymer (available from Smith and Nephew under the trademark Op-Site) is mounted in a stainless steel reactor, 0.10 g of benzocaine is added to the reactor, and the reactor is closed and pressurized with carbon dioxide to 175.775 $kg/cm^2$, while raising the temperature to 60° C. After three hours the reactor is cooled and de-pressurized. Part of the film is analyzed for benzocaine by extraction with methanol and examination by ultra-violet spectroscopy and is found to contain 5.52% benzocaine.

A 2.5 cm square portion of the film is mounted on release paper and submerged in 50 ml. 0.9% aqueous NaCl solution at room temperature for 47 hours with constant stirring. At various times portions of the aqueous solution are withdrawn and examined by ultraviolet spectroscopy (change in absorption of the solution at 285 nm) to determine the concentration of benzocaine in the aqueous phase. The results are summarized in FIG. 1 and 2. After 24 hours, equilibrium is reached and the distribution coefficient (i.e., $K_d$=drug concentration in aqueous solution/original concentration in the film) of benzocaine between the aqueous phase and the film is found to be 0.004.

EXAMPLE 2

A crosslinked polydimethylsiloxane membrane, reinforced with a knit polyester fabric, is impregnated with benzocaine using supercritical carbon dioxide as in EXAMPLE 1. The product film contains 0.81% benzocaine, which is desorbed into 10 ml of aqueous saline at a rate similar to that seen in EXAMPLE 1. Essentially all benzocaine is desorbed from the film.

EXAMPLE 3

The membrane used in EXAMPLE 2 is impregnated with hydrocortisone using supercritical carbon dioxide as in EXAMPLE 1. The hydrocortisone is desorbed into 10 ml of aqueous saline at a rate similar to that shown in EXAMPLE 1. The distribution coefficient of hydrocortisone between the aqueous phase and the film is $>0.32$, indicating diffusion of most of the hydrocortisone into the aqueous phase.

EXAMPLE 4

An aliphatic Polyurethane film (available under the trademark Tecoflex EG-93A from Thermedics, Inc.) is submerged in a solution of 400 ppm benzocaine in 0.9% aqueous NaCl along with about 250 mg solid benzocaine. The aqueous solution is stirred at room temperature for about 12 days and the film removed from the aqueous phase, rinsed, and dried. The film is found to contain 15.3% benzocaine by ultraviolet spectroscopy.

Figure 2:
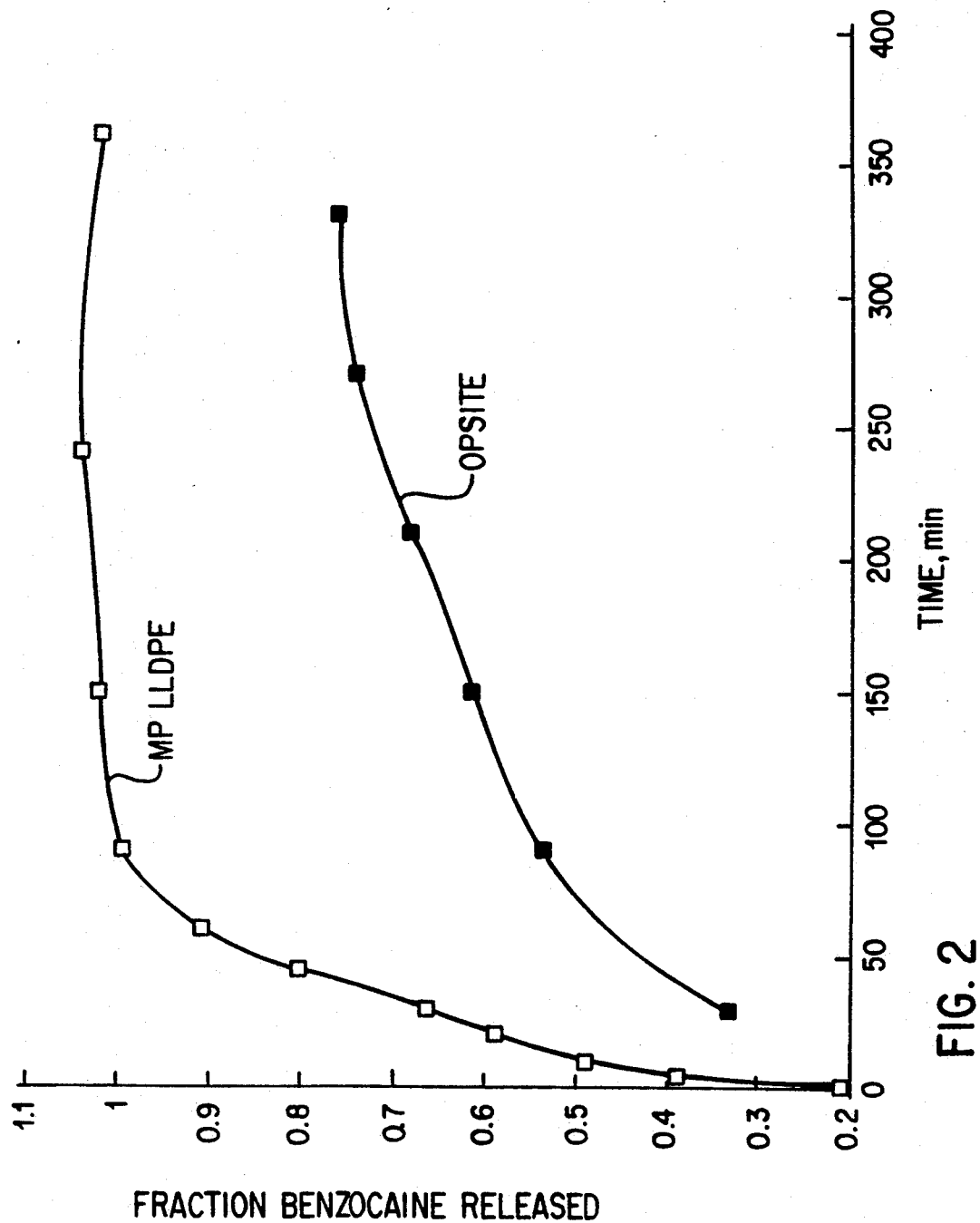

A portion of the impregnated film is placed in a 0.9% NaCl solution and the rate of diffusion of benzocaine from the film is recorded in FIG. 1. The final distribution coefficient is 0.045.

EXAMPLE 5

The procedure set forth in EXAMPLE 4 is repeated using 0.2113 g of an aromatic/aliphatic polyurethane film (available from J. P. Stevens, Inc. under the name MP1882). The rate of diffusion of benzocaine from the film is similar to that seen in EXAMPLES 1 and 4, with a final distribution coefficient of 0.0027.

EXAMPLE 6

Microporous, low density polyethylene (LLDPE) film (having a moisture vapor transmission rate=48 g/m$^2$/24 hr at 22.8° C. and 50% RH; gas permeability: oxygen $0.75 \times 10^5$ cc/m$^2$/day/atm, nitrogen=$0.43 \times 10^5$ cc/m$^2$/day/atm) (2.6 cm $\times$ 2.6 cm, 0.1479 g) is soaked in a 1% solution of benzocaine in isopropanol and allowed to stand for 30 minutes at room temperature, removed, blotted dry, and weighed. Weight recorded is 0.2674 g, which corresponds to 9.432 mg/g dry film, or 0.206 mg benzocaine/cm$^2$ of dry film. The impregnated film is placed in a 0.9% NaCl solution and the rate of release of benzocaine is monitored. Within 90 minutes, 98% if the benzocaine in the film is released to the solution and all of the benzocaine is released within 2 hours. At equilibrium there is no benzocaine in the film. The results of the release rates are recorded in FIG. 2 in comparison with the film of EXAMPLE 1.

EXAMPLE 7

The procedure of EXAMPLE 1 is repeated using the following films: microporous polyurethane having a vapor transmission rate=1000 g/m$^2$/24 hr at 22.8° C. and 50% RH and air permeability=$2 \times 10^5$ cc/m$^2$/day/atm (available under the trademark Porelle from Marand Marketing Internation, Inc.); reinforced silicone elastomer having a vapor transmission rate=48 g/m$^2$/24 hr at 22.8° C., oxygen permeability=$0.75 \times 10^5$ cc/m$^2$/day/atm, and nitrogen permeability=$0.43 \times 10^5$ cc/m$^2$/day/atm (available under the trademark Silastic 501-3 from Dow Corning Corp.); and a medical grade, nylon mesh reinforced, adhesive-backed, transparent aliphatic polyerethane film having a weight of 0.51 g/m$^2$, an elongation of 40–45%, and a thickness of 0.0254 mm without mesh and 0.1778 mm with mesh, semi-occlusive to water vapor, oxygen, and carbon dioxide, and occlusive to water, urine, bacteria, and feces.

EXAMPLE 8

The film in EXAMPLE 1 is impregnated with 5% isosorbide dinitrate (based on film weight) using the procedure of EXAMPLE 1. The impregnated film is applied to a stage 2 pressure sore (broken epidermis with distinct edges blending into tan indistinct area of redness, heat, and induration) on the left greater trochanter. The dressing is replaced every 3–5 days until the lesion heals and redness disappears.

EXAMPLE 9

Triethanolamine salicylate is impregnated into various polyurethane films. Using the procedure in EXAMPLE 1 triethanolamine salicylate as active ingredient is incorporated into the films described in EXAMPLES 1, 4, and 5. The film described in EXAMPLE 1 contains 14.3% active ingredient, the film described in EXAMPLE 4 contains 2.65% active ingredient, and the film described in EXAMPLE 5 contains 3.4% active ingredient.

What is claimed is:

1. A dry bandage comprising a gas- and moisture-permeable, flexible thermoplastic film impregnated with a pharmaceutical that is releasable from the film into a lesion upon application thereto wherein the thermoplastic film is impregnated with the pharmaceutical by contacting the film with the pharmaceutical dissolved in a liquefied gas maintained at supercritical conditions.

* * * * *